(12) United States Patent
Allwohn et al.

(10) Patent No.: US 6,372,203 B1
(45) Date of Patent: Apr. 16, 2002

(54) HAIR TREATMENT COMPOSITIONS WITH POLYMERS MADE FROM UNSATURATED SACCHARIDES, UNSATURATED SACCHARIC ACIDS OR THEIR DERIVATIVES

(75) Inventors: Juergen Allwohn, Burgschwalbach; Susanne Birkel, Rossdorf, both of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/562,214

(22) Filed: Apr. 28, 2000

(30) Foreign Application Priority Data

Apr. 30, 1999 (DE) .......................................... 199 19 785

(51) Int. Cl.⁷ .......................... A61K 7/06; A61K 7/075; A61K 7/08
(52) U.S. Cl. ................ 424/70.13; 424/70.1; 424/70.11; 424/70.12; 424/70.22; 424/70.27; 424/70.21; 424/70.31; 424/70.9
(58) Field of Search .............................. 424/70.1, 70.11, 424/70.13, 47, 70.12, 70.22, 70.27, 70.21, 70.31, 70.9

(56) References Cited

FOREIGN PATENT DOCUMENTS

| DE | 42 21 381 C1 | 2/1994 |
|----|----|----|
| EP | 0 412 704 B1 | 4/1999 |
| WO | 95/25135 | 9/1995 |
| WO | 99/00436 | 1/1999 |

OTHER PUBLICATIONS

Abstract in English for WO 95/25135 A1 (1995).*
Abstract in English for WO 99/00436 A2 (1999).*
Definition for foundation, from Merriam–Webster Online (2001).*

* cited by examiner

Primary Examiner—Thurman K. Page
Assistant Examiner—Brian K. Seidleck
(74) Attorney, Agent, or Firm—Michael J. Striker

(57) ABSTRACT

A hair treatment composition contains one or more polymers or copolymers, each of which is made from one or more monomers, in a cosmetic foundation. The respective monomers are selected from the group consisting of ethylenic unsaturated saccharides, ethylenic unsaturated saccharic acids, derivatives of ethylenic unsaturated saccharides and derivatives of ethylenic unsaturated saccharic acids. The unsaturated sachharides and saccharic acids are present in cyclic or open chain form.

11 Claims, No Drawings

HAIR TREATMENT COMPOSITIONS WITH POLYMERS MADE FROM UNSATURATED SACCHARIDES, UNSATURATED SACCHARIC ACIDS OR THEIR DERIVATIVES

BACKGROUND OF THE INVENTION

1. Field of the Invention

The subject matter of the present invention is a hair treatment composition containing at least one polymer or copolymer made from unsaturated saccharides, unsaturated saccharic acids or their derivatives.

2. Prior Art

A pleasing appearance has always been considered very important. Hair style plays a special role in providing that pleasing appearance. Well-styled and conditioned hair is the basis for a pleasing appearance. Pleasant feel, elasticity, volume, luster and hold should be enumerated among the requirements which are established for well-styled hair. There are an entire series of hair treatment agents, such as shampoos, care compositions, rinses, sprayed liquids, which are applied in a wide variety of different applications, for example as leave-on or as rinse-off products, for cleaning and care of the hair. Three other product categories have been used besides these care products. These product categories are permanent or temporary hair dye compositions, permanent hair shaping compositions in the form of mildly alkaline or acidic permanent wave or hair curling compositions, and compositions, which permit only temporary shaping and stabilizing of the hair style and generally are known as styling agents. For that purpose numerous products, such as hair sprays, hair lacquers, fixing lotions, fixing foams, hair gels, luster-producing products, styling creams, etc, are available. All these compositions have in common that they are made from a number of individual substances or ingredients, which fulfill different purposes according to their formulation.

Polymers, which according to their structure have hair care and/or hair fixing properties, which influence the product consistency positively, improve the transport and adherence of the active ingredients to the hair or modify the properties of the remaining ingredients advantageously, are of special significance. Polymers, which are based on recycled raw materials and have good biodegradability, are also of special significance. An additional protective effect, e.g. protection of the hair from drying out or regulation of the moisture content of the hair by providing an improved water retention capability by means of polymers sheathing the hair, is especially desirable.

SUMMARY OF THE INVENTION

It is an object of the present invention to provide a new class of polymers of this type, which fulfill one or more of the above-described desirable functions.

These new polymers, which are described in more detail in the following, are made from unsaturated saccharides, saccharic acids or their derivatives. They are advantageously useable in a number of different hair treatment compositions.

According to the invention the hair treatment composition comprises at least one polymer or copolymer, which is built up from at least one monomer, which is selected from the group consisting of
(a) ethylenic unsaturated saccharides and their derivatives, and
(b) ethylenic unsaturated saccharic acids and their derivatives; and a suitable cosmetic foundation, in which the unsaturated saccharides and saccharic acids can be present in cyclic or open-chain form. Also mixtures of polymers or copolymers can be used. The term "derivative" means a compound in which the acid groups are present as salts, esters, lactones, amides, imides or nitrites or in which the hydroxy groups are present in alkylated or acylated form or provided with common protective groups and compounds, which fall under one of the below-named general formulas I to XVII. The term "derivative" also means hexenitols or pentenitols derived by water cleavage from hexitols and pentitols. The hexenitols or pentenitols can also be present in the form of cyclic ethers or in linear form, in which the hydroxyl groups can be provided with conventional protective groups or a keto group can be contained in the molecule.

The cosmetic composition according to the invention preferably contains from 0.01 to 25 percent by weight, especially preferably from 0.05 to 10 percent by weight, of the polymers and copolymers according to the invention derived from the saccharides.

The polymers can be made by radical polymerization of ethylenic unsaturated mono-, di- or oligosaccharides, hexenitols, pentenitols or their derivative compounds, which contain at least one ethylenic double bond in a ring (endocyclic), at the ring (exocyclic) or in open chain form. The unsaturated saccharides or saccharic acids can be chemically protected or unprotected, or enzymatically or chemically modified.

Suitable polymers and copolymers and their manufacture are described in WO 95/25135 and in WO 99/00436. The polymers and copolymers described there are incorporated in this disclosure by reference. Suitable monomers derived from unsaturated saccharides have the following general formulae I to X:

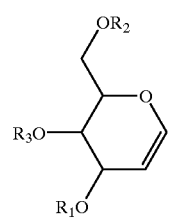

I

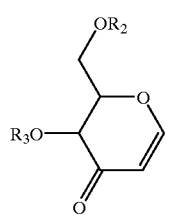

II

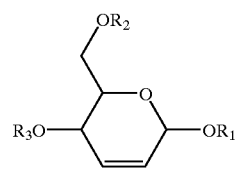

III

-continued

IV
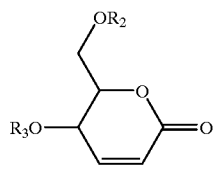

V
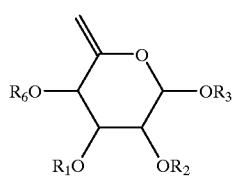

VI
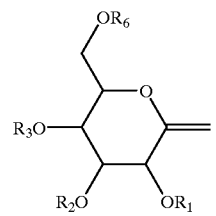

VII
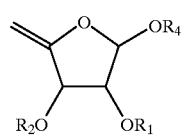

VIII
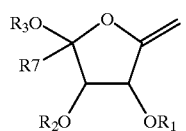

IX
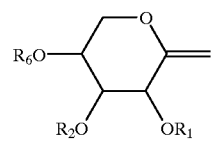

X
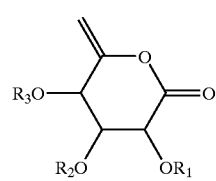

Suitable monomers derived from unsaturated saccharic acids are those of the general formulae XI to XVII:

XI
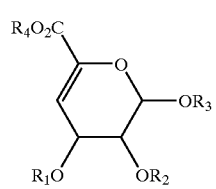

-continued

XII
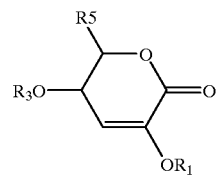

XIII
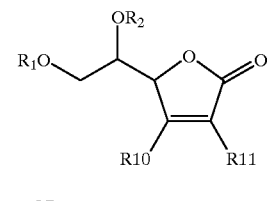

XIV
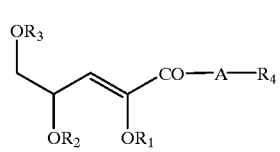

XV
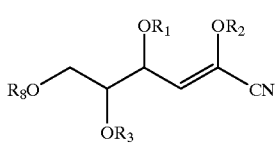

XVI
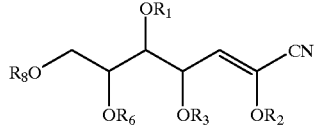

XVII wherein $R_1$, $R_2$, $R_6$ and $R_8$, independently of each other, represent a hydrogen, alkyl, aralkyl, acyl or silyl group or each pair of the foregoing groups represent a common alkylidene group in a suitable spatial configuration; $R_3$ represents one of the foregoing groups or stands for glycosyl; $R_4$ and $R_9$ represent hydrogen, alkyl or a suitable counter ion; $R_5$ represents hydrogen, $CH_2OR_8$ or $COOR_9$; $R_7$ stands for hydrogen or O-glycosyl; $R_{10}$ and $R_{11}$ represents, independently of each other, a hydroxyl, acetamido, O-acyl or O-alkyl group and A stands for oxygen, an NH group or an N-alkyl group. The foregoing alkyl groups preferably contain from 1 to 24, especially preferably from 1 to 6, carbon atoms.

The saccharide and saccharic acid monomers or their derivative compounds can be copolymerized with one or more radically polymerizable, comonomers not derived from saccharides, especially vinyl monomers. The comonomers can be hydrophilic or hydrophobic, nonionic, cationic, anionic zwitterionic or amphoteric. The solubilizing, filmforming, hair fixing and hair care properties of the resulting copolymers can be adjusted by suitable choice of the type and amount of the comonomers. Preferably the hydrophilic monomers derived from saccharides can be combined with hydrophobic comonomers.

Suitable nonionic comonomers, for example, are acrylamide, methacrylamide, alkyl and dialkylacrylamides, alkyl and dialkylmethacrylamides, ethylenic unsaturated esters of $C_3$- to $C_{10}$-carboxylic acids (e.g. alkylacrylates or alkylmethacrylate), maleic acid dialkyl esters, vinylcaprolactone, five to eight membered N-vinyllactams, which can be substituted with up to 3 $C_1$- to $C_{12}$-alkyl groups on the ring, especially vinyl pyrrolidone and vinyl caprolactam, additional vinyl alcohols and vinyl esters (e.g. vinyl acetates or vinyl propionate), styrene, which can be substituted by one or two $C_1$- to $C_3$-alkyl groups on the aromatic ring. The alkyl groups of these monomers are preferably $C_1$- to $C_7$-alkyl groups, especially preferably $C_1$- to $C_3$-alkyl groups. Additional suitable nonionic copolymerizable groups include silicone macromers with a terminal ethylenic unsaturated group, such as described, for example, in EP 0 412 704. The unsaturated silicone macromers have the general formula $X—(Y)_n—Si(R)_{3-m}(Z)_m$, wherein X represents a vinyl group, Y, a divalent connecting group, R represents a hydrogen, alkyl, aryl or alkoxy group and Z represents a monovalent polysiloxane group with a molecular weight of at least 500 and n stands for 0 or 1 and m stands for 1, 2 or 3. The foregoing alkyl groups preferably contain from 1 to 24, especially preferably from 1 to 6, carbon atoms.

Suitable anionic comonomers include those monomers that are anionizable by neutralization of an acidic group. Suitable anionic comonomers include, for example, monoethylenic unsaturated $C_3$- to $C_{10}$-carboxylic acids and their alkali metal, alkaline earth metal or ammonium salts, such as acrylic acid, methacrylic acid, dimethylacrylic acid, ethylacrylic acid, vinylacetic acid, allylacetic acid, vinylpropionic acid, crotonic acid, maleic acid or maleic acid anhydride or maleic acid monoester.

Cationic comonomers include those monomers, which are cationizable by protonation of basic nitrogen. Suitable cationic comonomers are, for example, those monomers which have cationic or cationizable groups, preferably primary, secondary, tertiary or quaternary nitrogen groups. Suitable ammonium-substituted vinyl monomers are, for example, trialkylmethacryloxyalkylammonium, trialkylacryloxyalkylammonium, dialkyldiallylammonium, quaternary vinylammonium monomers with cyclic, cationic nitrogen-containing groups, such as pyridinium, imidazolium or quaternary pyrrolidone, e.g. alkylvinylimidazolium, groups, which can be substituted on the heterocyclic ring with up to 3 $C_1$- to $C_{12}$-alkyl substituted groups, alkylvinylpyridinum or alkylvinylpyrrolidone salts. Suitable amine substituted vinyl monomers are, for example, dialkylaminoalkylacrylate, dialkylaminoalkylmethacrylate, monoalkylaminoalkylacrylate and monoalkylaminoalkylmethacrylate, N-vinylimidazoles, which can be substituted on the ring with up to 3 $C_1$- to $C_{12}$-alkyl groups. The alkyl groups of these monomers preferably are lower alkyl groups, for example $C_1$- to $C_7$-alkyl groups, especially preferably $C_1$- to $C_3$-alkyl groups.

Zwitterionic or amphoteric comonomers contain both basic or cationic groups and also acidic or anionic groups. Suitable monomers with zwitterionic groups contain the functional group $—NR_1R_2^+—A—COO^-$, wherein $R_1$ and $R_2$, independently of each other, represent alkyl groups with 1 to 24, preferably 1 to 4 carbon atoms and A represents a divalent connecting group, for example an alkylene group with 1 to 24, preferably 1 to 4, carbon atoms, wherein the groups $R_1$ and $R_2$ are connected with each other so that they form a ring containing the N atom, which is preferably a six membered ring. Methacryloylethylbetaine is a preferred monomer.

The polymers or copolymers to be used according to the invention can be coupled with polyethylene glycol or polypropylene glycol chains by free hydroxyl groups. The polymers obtained using the unsaturated lactones can be converted into anionic polymers after neutralization or by hydrolysis of the lactone group in acid.

The saccharide polymers to be used according to the invention are characterized by a high affinity for hair. They are deposited on the hair and because of that strengthen the hold of the hair style. When one puts the saccharide polymers in typical hair care composition, such as lotions, foams, liquids or foam fixing agents, hair treated with these hair care compositions is satisfactorily fixed and springy in the dry state but simultaneously has a good feel. The saccharide polymers are characterized by a high moisture up-take and by a high moisture retention. They can therefore control the moisture content of the hair or are advantageously used to protect the hair from drying out. The improved moisture up take and improved moisture retention are also observed with films formed from combinations of the saccharide polymers with conventional film-forming polymers. It is especially preferably to form and use combinations of saccharide polymers with those conventional film-forming polymers, which when used alone form a hard brittle film and are characterized by scarcely any or only very small moisture up-take and moisture retention.

The subject matter of the invention also includes a hair treatment composition containing (A) at least one polymer or copolymer according to the foregoing disclosure derived from saccharides or saccharic acids or their derivatives; and (B) at least one film-forming polymer, in a suitable cosmetic foundation.

The film-forming polymers (B) are used in these hair treatment compositions preferably in an amount of from 0.01 to 25, especially preferably in an amount of from 0.1 to 20, percent by weight, alone or in a mixtures with each other. The term "film-forming polymer" means that polymer which is in a position to deposit a polymer film on the hair. The film-forming polymers can be nonionic, cationic, anionic, zwitterioinic or amphoteric and of synthetic or natural origin.

Suitable anionic polymers include synthetic homopolymers or copolymers with monomer units containing neutralizable acidic group, which are necessarily copolymerizable with comonomers, which contain no acidic groups. The acidic groups can be sulfonic acid groups, phosphoric acid groups and carboxylic acid groups. The carboxylic acid groups are preferred. Suitable monomers containing acidic groups include, for example, acrylic acid, methacrylic acid, crotonic acid, maleic acid or maleic acid anhydride, aldehydocarboxylic acids or ketocarboxylic acids.

Comonomers not substituted with acidic groups include, for example, acrylamide, methacrylamide, alkyl and dialkylacrylamide, alkyl and dialkylmethacrylamide, alkylacrylate, alkylmethacrylate, vinylcaprolactone, vinylpyrrolidone, vinyl ester, vinyl alcohol, propylene glycol or ethylene glycol, amine substituted vinyl monomers, such as dialkylaminoalkylacrylates, dialkylaminoalkylmethacrylates, monoalkylaminoalkylacrylates and monoalkylaminoalkylmetacrylates, in which the alkyl groups of these monomers are preferably $C_1$- to $C_7$-alkyl groups, especially preferably $C_1$- to $C_3$-alkyl groups.

Suitable anionic polymers are, especially, branched homopolymers of acrylic acid or methacrylic acid with polyfunctional agents, copolymers of acrylic acid or methacrylic acid with monomers selected from the group consisting of acrylic acid or methacrylic acid esters, acrylamides, methacrylic amides and vinylpyrrolidones, homopolymers of crotonic acids and copolymers of crotonic acid with monomers selected from the group consisting of vinyl esters, acrylic acid or methacrylic acid esters, acrylamides and methacrylamides. A suitable natural anionic polymer is for example partially or completely neutralized shellac.

Preferred polymers with acid groups are cross-linked or noncross-linked vinyl acetates/crotonic acid copolymers, which, for example, are marketed in the form of a 60% solution in isopropanol/water under the trademark ARISTOFLEX® by HOECHST, Germany, and under the trademark LUVISET® CA-66 by BASF. Other suitable anionic polymers are, for example, terpolymers of vinyl acetate, crotonic acid and polyethylene oxide as well as terpolymers of acrylic acid, alkyl acrylates and N-alkylacrylamides, especially acrylic acid/ethylacrylate/N-t-butylacrylamide terpolymers, such as those marketed under the trademark ULTRAHOLD® 8 and ULTRAHOLD® STRONG by BASF, Germany, or terpolymers of vinyl acetate, crotonate and vinyl alkanoate, especially vinyl acetate/crotonate/vinyl neodecanoate copolymers, such as those e.g. marketed under the trademark REYSN 28-2930®.

Anionic polyurethanes are an additional class of suitable anionic polymers. Preferred polyurethanes are characterized in that they (a) have terminal acid groups, which, for example, are introduced by aminosulfonic acids or aminocarboxylic acids, (b) if needed, contain additional free carboxylic acid groups, which are introduced by polymerizing in carboxylic acid diols, such as dimethylolpropanoic acid as a comonomer and (c) contain polyurethane sequences, which were formed from polyesterdiols and diisocyanates, such as alkylene diisocyanates or isophorone diisocyanate. Luviset® PUR of BASF, Germany, is especially suitable.

The anionic polymers in the compositions according to the invention are neutralized partially or completely with a cosmetically compatible neutralization agent. Organic or inorganic bases are used as the neutralization agents. For example, bases, such as aminoalkanols, like e.g. aminomethylpropanol (AMP), triethanolamines or monoethanolamines, also ammonia, NaOH, among others, are suitable.

Suitable synthetic, nonionic film-forming hair-fixing polymers are, e.g., homo- or copolymers, which are built up from at least one nonionic monomer, such as acrylamide, methacrylamide, alkyl- and dialkylacrylamides, alkyl- and dialkylmethacrylamides, alkylacrylates, alkylmethacrylates, vinyl caprolactone, vinyl pyrrolidone, vinyl esters, vinyl alcohols, propylene glycols or ethylene glycols, in which the alkyl groups of these monomers are preferably $C_1$- to $C_7$-alkyl groups, especially preferably $C_1$- to $C_3$-alkyl groups. Suitable synthetic, nonionic film-forming hair-fixing polymers are, for example, homopolymers of N-vinylformamides and homopolymers of vinylpyrrolidones. Additional suitable synthetic film-forming nonionic hair-fixing polymers are, for example, copolymerizates from vinyl pyrrolidone and vinyl acetate, terpolymers of vinyl pyrrolidone, vinyl acetate and vinyl propionate, polyacrylamides, polyvinyl alcohols or polyethylene glycols with a molecular weight of from 800 to 20,000 g/mol.

Suitable natural film-forming polymers are, for example, chitosan with a molecular weight of 20,000 up to about 5 million g/mol, as marketed, e.g., by Pronova, or different saccharide types, such as polysaccharides or mixtures of oligo-, mono- and disaccharides, which are marketed under the trademark C-PUR® by Cerestar, BrCissels, Belgium. Additional suitable natural polymers are Chinese pine resin and cellulose derivative compounds, for example hydroxypropyl cellulose with a molecular weight of 30,000 to 50,000 g/mol.

Suitable film-forming cationic polymers are characterized by being built up from at least one type of monomer, which contains cationic groups or cationizable groups, preferably primary, secondary, tertiary or quaternary nitrogen groups. Suitable ammonium-substituted vinyl monomers are, for example, trialkylmethacryloxyalkylammonium, trialkylacryloxyalkylammonium, dialkyldiallylammonium quaternary vinylammonium monomers with groups containing cyclic cationic nitrogen, such as pyridinium, imidazolium or quaternary pyrrolidone, e.g. alkylvinylimidazolium which can be substituted with up to three $C_1$- to $C_{12}$-alkyl groups on the heterocyclic ring, alkylvinylpyridinium, or alkylvinyl pyrrolidone salts. Suitable amine-substituted vinyl monomers are, for example, dialkylaminoalkylacrylates, dialkylaminoalkylmethacrylates, monoalkylaminoalkylacrylates and monoalkylaminoalkylmethacrylates, N-vinylimidazoles, which can be substituted with up to three $C_1$- to $C_{12}$-alkyl groups on the ring. The alkyl groups of these monomers preferably are lower alkyl groups, such as $C_1$- to $C_7$-alkyl groups, especially preferably $C_1$- to $C_3$-alkyl groups. The cationic and/or basic monomers can be copolymerized with non-cationic and/or non-basic comonomers.

Suitable cationic polymers are, for example, polyvinylpyrrolidone/dimethylaminoethylmethacrylate copolymer, a copolymer of polyvinylpyrrolidone and imidazolimine methochloride, a terpolymer made from dimethyldiallylammonium chloride, sodium acrylate and acrylamide, a terpolymer made from vinylpyrrolidone, dimethylaminoethylmethacrylate and vinylcaprolactam, hydroxyethylcellulose substituted with quaternary ammonium groups, vinylpyrrolidone/methacrylamidopropyltrimethylammonium chloride copolymer or diquaternary polydimethylsiloxanes (INCI: Quaternium-80).

Suitable amphoteric polymers include those containing cationic groups or groups that are catonizable by protonation and anionic groups or groups that are anionizable by deprotonation. The cationic groups can, for example, be quaternary amine groups and the groups that are catonizable are, for example, primary, secondary or tertiary amine groups. The anionic groups can be carboxylate, sulfate, sulfonate, phosphate or phosphonate groups. The anionizable groups include, for example, the protonate form of the foregoing anionic groups.

Suitable amphoteric polymers are, for example, copolymers made from octylacrylamide, t-butylaminoethylmethacrylates and two or more monomers, made from acrylic acid, methacrylic acid or their esters. Additional examples include, for example, copolymers of acrylic acid, methacrylate and methacrylamidopropyltrimethylammonium chloride (INCI: polyquaternium-47), copolymers made from acrylamidopropyltrimonium chloride and acrylates or copolymers of acrylamides, acrylamidopropyltrimonium chloride, 2-aminopropylacrylamidsulfonate and DMAPA (INCI: polyquaternium-43).

The compositions according to the invention can also contain additive ingredients usually used for hair treatment composition, for example cationic combability-improving agents, oils, silicone oils, thickeners and other ingredients. Similarly the compositions can contain consistencyimparting substances, such as are usually used for creams, such as fatty alcohols, fatty alcohols sulfates or fatty alcohol ether sulfates. Similarly polyethylene glycols that are liquid, waxy or solid at room temperature can be included in the compositions of the invention. Understandably the compositions according to the invention can also contain additional cosmetic additive ingredients, such as thickening polymers and their combinations in an amount of preferably from 0.01 to 15 percent by weight; perfume oils, in an amount of from 0.01 to 5 percent by weight; turbidity-inducing agents, such as e.g. ethylene glycol distearate, styrene/PVP copolymer or polystyrene, in an amount of preferably from 0.01 to 5 percent by weight; wetting agents, surfactants or emulsifiers with or without washing activity from the classes of nonionic, anionic, cationic or amphoteric surface-active substances, such as fatty alcohol sulfates, ethoxylated fatty alcohols, fatty acid alkanolamides, such as esters of hydrogenated castor oil fatty acids, in an amount of preferably from 0.1 to 20 percent by weight; further moisture retention agents, dyes, light protective agents, antioxidants, luster-imparting agents and preservatives, in an amount of preferably from 0.01 to 10 percent by weight. Suitable soluble or insoluble silicone polymers are suitable as additional additives in an amount of from 0.01 to 50 percent by weight, preferably in concentrations of 0.1 to 5 percent by weight.

The compositions of the invention can have different application forms, e.g. they can be in the form of hair care compositions, hair fixing compositions, hair cleaning compositions, hair dye compositions and tinting compositions. The composition can be applied as a lotion, foam, milk, gel, cream, gel-foam, aerosol or non-aerosol spray, hair wax or in the form of a hair care emulsion (hair rinse, conditioner). The composition can also be provided with anionic, amphoteric, nonioinic or cationic surfactants so that it is a shampoo or with direct-dyeing dye compounds or oxidative hair dye precursor compounds as a hair dyeing composition, e.g. a dyeing fixer. A composition according to the invention in the form of a non-rinsable leave-on-product is especially preferred.

If the hair treatment composition according to the invention is an aerosol spray, it also contains from 15 to 85 percent by weight, preferably 25 to 75 percent by weight, of a propellant and is filled in a pressurized container. The propellant can be, for example, a lower alkane, such as n-butane, i-butane and propane, or their mixtures, and dimethyl ether or a fluorocarbon, such as F152a (1,1-difluoroethane) or F134 (tetrafluoroethane) and/or also a gaseous propellant, such as $N_2$, $N_2O$ and $CO_2$, or their mixtures.

When the hair treatment composition is a sprayable non-aerosol hair spray, it is sprayed with the help of a suitable mechanically operated spraying device. The term "mechanical spraying device" means a device that permits spraying of a liquid without using a propellant. For example, a spray pump and an elastic container provided with a spraying valve, in which the cosmetic composition according to the invention is filled under pressure so that the container stretches and the composition is continuously dispensed from the container because of contraction of the elastic container when the spray value is opened, are both suitable as the mechanical spraying device.

When the hair treatment composition according to the invention is a foam composition (mousse), it contains at least one conventional foam-forming substance. The composition is foamed with or without the aid of a propellant gas or a chemical propellant and is worked into the hair as foam and loads the hair without being rinsed out. An apparatus for foaming the composition can be provided for the composition according to the invention as an additional component. The term "apparatus for foaming" means those devices which permit foaming of a liquid with or without use of a propellant. For example, a commercial foam pump can be used as a suitable mechanical foam device or an aerosol foam head can be used.

When the hair treatment composition according to the invention is a hair gel, it also contains at least one gel-forming substance, for example one of the above-mentioned thickening ingredients in an amount of preferably from 0.05 to 10, especially preferably from 0.1 to 2, percent by weight. The viscosity of the gel amounts to preferably from 500 to 50,000 cSt, especially preferably from 1,000 to 15,000 cSt at 25° C. (measured with a rotary viscosity meter according to DIN 53 018 T1 u.2).

When the hair treatment composition according to the invention is a hair wax, it also contains a water-insoluble fatty or waxy material, or water-insoluble materials that impart a wax-like consistency to the composition, in an amount of preferably from 0.5 to 30 percent by weight. Emulsifiers, for example, with an HLB value under 7, such as silicone oils, silicone waxes, wax (e.g. alcohol waxes, waxy acids, waxy esters and especially natural waxes, such as bees wax, caranauba wax, etc), fatty alcohols, fatty acids, fatty acid esters or high molecular weight polyethylene glycols with a molecular weight of from 800 to 20,000 g/mol, preferably from 2,000 to 10,000 g/mol, are suitable as the water-insoluble materials.

When the hair treatment composition according to the invention is present as a hair lotion, it is present in the form of a low viscosity or substantially non-viscose solution, a dispersion or an emulsion with a content of at least 10 percent by weight, preferably 20 to 95 percent by weight, of a cosmetically compatible alcohol. Especially lower alcohols having 1 to 4 carbon atoms commonly used for cosmetic purposes, especially isopropanol and ethanol, are suitable for this application.

When the hair treatment composition according to the invention is a hair cream, it is preferably present as an emulsion and contains either additional viscosity-imparting ingredients, such as the above-described thickeners in an amount of from 0.1 to 10 percent by weight or the required viscosity and creamy consistency is built up by micelle formation with the aid of suitable emulsifiers, fatty acids, fatty alcohols, waxes, etc in the usual manner.

If the cosmetic composition according to the invention is used for hair care or hair fixing, it is applied in the following manner: After the hair is washed, 5 to 30 g of the composition are distributed on the hand towel dried hair. Subsequently the hair is combed and shaped into a hairstyle and dried.

When the composition according to the invention is a composition for permanent shaping of hair, it contains from 0.5 to 15 percent by weight of at least one keratin-reducing mercapto compound. It is preferably an aqueous, alkaline or weakly acidic preparation (pH 5 to 10), which contains cysteine, cysteamine, N-acetyl-L-cysteine, mercaptocarboxylic acid, such as thioglycolic acid or thiolactic acid, or salts of mercaptocarboxylic acids, such as ammonium- and guanidine salts of thioglycolic acid or thiolactic acid.

If the composition according to the invention is a hair toning composition, it contains from 0.05 to 2.0 percent by weight of at least one direct-dyeing hair dyestuff, which can be selected from the following classes of dye compounds that directly dye the hair: aromatic nitro dye compounds, for example 1,4-diamino-2-nitrobenzene; azo dye compounds, for example Acid Brown 4 (C.I. 14 805); anthraquinone dye compounds, for example, Disperse Violet 4 (C.I. 61 105), triphenylmethane dye compounds, for example Basic Violet 1 (C.I. 42 535), and/or natural hair dye compounds, such as Henna or Reng, which may not require oxidation to develop color. These dye compounds have acidic, nonionic or basic character according to the nature of their substituent groups.

The following example illustrate the invention in detail, but those details should not be considered as limiting the appended claims.

EXAMPLES

The following polymers derived from unsaturated saccharides were used in the examples:

| Polymer (1) | Copolymer, obtained by polymerization of 3,4,5-tri-O-benzoyl-1-deoxy-2,6-anhydro-D-fructose-hex-1-enitol and maleic acid anhydride analogous to example 29 or WO 95/25135 with subsequent hydrolysis of the benzoyl groups and the anhydride. |
|---|---|
| Polymer (2) | Copolymer of 2,4,6-tri-O-acetyl-3-deoxy-D-erythro-hex-2-enono-1,5-lactone and vinyl acetate in a ratio of 21:79, made analogous to example 5 of WO 99/00436. |
| Polymer (3) | Copolymer of 2,4,6-tri-O-acetyl-3-deoxy-D-erythro-hex-2-enono-1,5-lactone and vinyl pyrrolidone in a ratio of 45:55, made analogous to example 5 of WO 99/00436. |
| Polymer (4) | Copolymer of 2,4,6-tri-O-acetyl-3-deoxy-D-erythro-hex-2-enono-1,5-lactone and butyl vinyl ether in a ratio of 50:50, made analogous to example 5 of WO 99/00436. |

Example 1

Measurement of Moisture Absorbtivity

Five solutions were prepared with the following polymer composition:

A) 1% by weight saccharide polymer (1)

B) 5% by weight octylacrylamide/acrylates/butylaminoethylmethacrylate Copolymer (Amphomer®)

C) 5% by weight Amphomer® +0.05% by weight saccharide polymer (1)

D) 5% vinyl pyrrolidone/vinyl acetate copolymer (Luviskol® VA 37)

E) 5% by weight Luviskol® VA37+1% by weight saccharide polymer (1)

The determination of moisture absorbtivity was performed three times for each solution. Weighing bottles were half-filled with a portion of each solution to be tested. The solvent was completely evaporated within 24 hours in a circulating dry box at 40° C. and the contents of the bottles were dried. After cooling the weighing bottles were kept for 48 hours in 31% relative humidity and 22° C. and subsequently were weighed. After that the weighing bottles were kept for 48 hours in 31% relative humidity and 22° C. and subsequently were weighed. From the difference of the weights of the respective bottles the moisture absorbtivity (WDA) was calculated. The results are shown in the following Table I.

TABLE I

THEORETICAL AND ACTUAL MOISTURE ABSORBTIVITY OF POLYMER FILMS
(residual moisture)

| Polymer | Actual WDA in % | Expected WDA in % for Additive Behavior |
|---|---|---|
| A | 137.7 ± 0.2 | — |
| B | 6.2 ± 0.2 | — |
| C | 25.0 ± 0.2 | 7.4 |
| D | 3.4 ± 0.2 | — |
| E | 29.7 ± 0.1 | 4.8 |

The polymer combinations C and E according to the invention have a considerably greater moisture absorbtivity than would be expected on the basis of the properties of the individual ingredients using an additivity principle.

Example 2: Hair Balm

| 0.50 g | saccharide polymer (2) |
|---|---|
| 6.00 g | glycerylstearate/polyethylene glycol (20)-cetearyl ether |
| 4.00 g | diquaternary polydimethylsiloxane (Abil ® Quat 3272) |
| 2.00 g | cetyl alcohol |
| 1.36 g | citric acid |
| 0.14 g | 1,2-dibromo-2,4-dicyanobutane |
| 0.12 g | perfume |
| to 100 g | water |

Example 3: Hair Rinse

| 0.75 g | saccharide polymer (3) |
|---|---|
| 4.00 g | cetylstearyl alcohol |
| 1.36 g | DL-2-pyrrolidon-5-carboxylic acid |
| 0.75 g | cetyltrimethylammonium chloride |
| 0.50 g | perfume |
| 0.20 g | plant extract Extrapon ® 5 Special of Dragoco, Germany |
| to 100 g | water |

Example 4: Sprayable Hair Care Composition

| 0.15 g | saccharide polymer (2) |
|---|---|
| 2.00 g | dimethyldiallylammonium chloride |
| 1.25 g | polyethyleneglycol(40) sorbitan monopalmitate |
| 1.00 g | DL-2-pyrrolidon-5-carboxylic acid |
| 0.10 g | perfume |
| 0.03 g | cetyltrimethylammonium chloride |
| 15.15 g | ethanol |
| to 100 g | water |

Example 5: Foam-form Hair Care Composition

| 0.40 g | saccharide polymer (3) |
|---|---|
| 2.00 g | cationic emulsion of amine functionalized polydimethylsiloxane (Dow Corning 929 cationic emulsion) |
| 1.30 g | citric acid |
| 0.50 g | hydroxypropylcellulose (MW = 1,150,000 g/mol) |
| 0.30 g | silicone wax Dow Corning 2501 cosmetic wax |
| 0.20 g | perfume |
| 0.25 g | cetyltrimethylammonium chloride |
| 0.15 g | D-panthenol |
| 0.10 g | elastin hydrolyzate |
| 5.00 g | propane/butane (5.0 bar) |
| 10.00 g | ethanol |
| to 100 g | water |

Example 6: Hair Fixing Composition

| 0.10 g | saccharide polymer (3) |
|---|---|
| 3.00 g | vinylpyrrolidone/vinyl acetate copolymer |
| 0.90 g | formic acid |
| 0.20 g | 1,2-propylene glycol |
| 0.15 g | perfume |
| 0.03 g | cetyltrimethylammonium chloride |
| 20.00 g | water |
| to 100 g | ethanol |

Example 7: Foam-Fixing Composition

| | |
|---|---|
| 0.25 g | saccharide polymer (3) |
| 3.15 g | polyvinylpyrrolidone |
| 1.60 g | citric acid |
| 0.60 g | hydrogenated castor oil, ethoxylated with 40 Mol ethyleneoxide |
| 0.22 g | decylpolyglucoside |
| 0.20 g | vinylpyrrolidone/methacrylamidopropyl-trimethylammonium chloride copolymer |
| 0.20 g | perfume |
| 6.00 g | propane/butane (5.0 bar) |
| to 100 g | water |

Example 8: Hair Spray Composition

| | |
|---|---|
| 0.05 g | saccharide polymer (3) |
| 3.50 g | vinyl acetate/crotonic acid/vinyl neodecanoate terpolymer |
| 0.15 g | perfume |
| 0.14 g | formic acid |
| 45.00 g | dimethyl ether |
| to 100 g | ethanol |

Example 9: 80% VOC Hair Spray

| | |
|---|---|
| 0.10 g | saccharide polymer (3) |
| 0.10 g | saccharide polymer (2) |
| 4.00 g | t-butyl acrylate/ethylacrylate/methacrylic acid terpolymer |
| 0.72 g | 2-amino-2-methyl-1-propanol |
| 0.20 g | cyclo-tetra(dimethylsiloxane) |
| 0.05 g | perfume |
| 15.00 g | water |
| 40.00 g | dimethyl ether |
| to 100 g | ethanol |

Example 10: 55% VOC Pump Spray

| | |
|---|---|
| 0.10 g | saccharide polymer (3) |
| 3.50 g | vinyl acetate/crotonic acid copolymer |
| 0.28 g | formic acid |
| 0.20 g | perfume |
| 55.00 g | ethanol |
| to 100 g | water |

Example 11: Hair Gel

| | |
|---|---|
| 0.20 g | saccharide polymer (2) |
| 2.50 g | hydroxypropylmethylcellulose |
| 0.80 g | polyoxyethylen-(20)-sorbitan monopalmitate |
| 0.50 g | polyoxyethylen-(25)-p-aminobenzoic acid |
| 0.40 g | formic acid |
| 0.12 g | cis-1-(3-chlorallyl)-3,5,7-triaza-1-azoniaadamantane chloride |
| 0.10 g | perfume |
| 23.00 g | glycerol (86 percent) |
| to 100 g | water |

Example 12: Dyeing-Fixing Composition

| | |
|---|---|
| 0.23 g | saccharide polymer (2) |
| 2.50 g | vinyl acetate/crotonic acid/polyglycol copolymer |
| 0.20 g | perfume |
| 0.07 g | 1-amino-4-(2',3'-dihydroxypropyl)amino-5-chloro-2-nitrobenzene |
| 0.05 g | Basic Brown 17 (C.I. 12 251) |
| 0.01 g | Basic Blue 7 (C.I. 42 595) |
| 0.0023 g | Basic Violet 14 (C.I. 42 510) |
| 50.00 g | ethanol |
| to 100 g | water |

Example 13: Permanent Shaping Composition

| | |
|---|---|
| 0.1 g | saccharide polymer (1) |
| 8.0 g | thioglycolic acid |
| 2.6 g | ammonium hydrogen carbonate |
| 0.3 g | glycerol polyethylene glycol-(35)-ricinoleate |
| 0.3 g | perfume |
| 0.1 g | octylphenol, ethoxylated with 20 Mol ethylene oxide |
| to 100 g | water |

Example 14: Permanent Shaping-Fixing Composition

| | |
|---|---|
| 0.5 g | saccharide polymer (4) |
| 10.0 g | sodium bromate |
| 3.2 g | disodium hydrogen phosphate dodecahydrate |
| 0.8 g | ortho-phosphoric acid (85%) |
| 0.5 g | monosodium phosphate |
| to 100 g | water |

Example 15: Foam-Fixing Composition

| | |
|---|---|
| 0.20 g | saccharide polymer (2) |
| 14.00 g | hydrogen peroxide (35%) |
| 3.41 g | o-phosphoric acid (85%) |
| 1.25 g | DL-2-pyrrolidon-5-carboxylic acid |
| 0.66 g | laurylaminodimethylacetobetaine |
| 0.50 g | polypropylen-(1)-polyethylen-(9)-laurylglycol ether |
| 0.20 g | perfume |
| 0.05 g | p-acetaminophenol |
| to 100 g | water |

All ratios and percentages, unless otherwise indicated, are weight ratios and percentages by weight.

The disclosure in German Patent Application 199 19 785.7-41 of Apr. 30, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair treatment composition containing at least one polymer or copolymer made from unsaturated saccharides, unsaturated saccharic acids or their derivatives, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment composition comprising a cosmetic carrier; and from 0.01 to 25% by weight of at least one polymer or copolymer made from at least one monomer, said at least one monomer being selected from the group consisting of ethylenic unsaturated saccharides, ethylenic unsaturated saccharic acids, derivatives of ethylenic unsaturated saccharides and derivatives of ethylenic unsaturated saccharic acids;

wherein said unsaturated sachharides and saccharic acids are present in cyclic or open chain form.

2. The hair treatment composition as defined in claim 1, wherein said unsaturated saccharides or saccharic acids have an ethylenic double bond present in endocyclic, exocyclic or in said open chain form.

3. The hair treatment composition as defined in claim 1, wherein said derivatives of said saccharic acids are selected from the group consisting of salts of the saccharic acids, esters of the saccharic acids, lactones of the saccharic acids, amides of the saccharic acids, imides of the saccharic acids and nitriles of the saccharic acids or wherein said derivatives of saccharic acids having hydroxy groups have protective groups for said hydroxy groups.

4. The hair treatment composition as defined in claim 1, wherein said at least one monomer is selected from the group consisting of compounds of the formulae I to XVII:

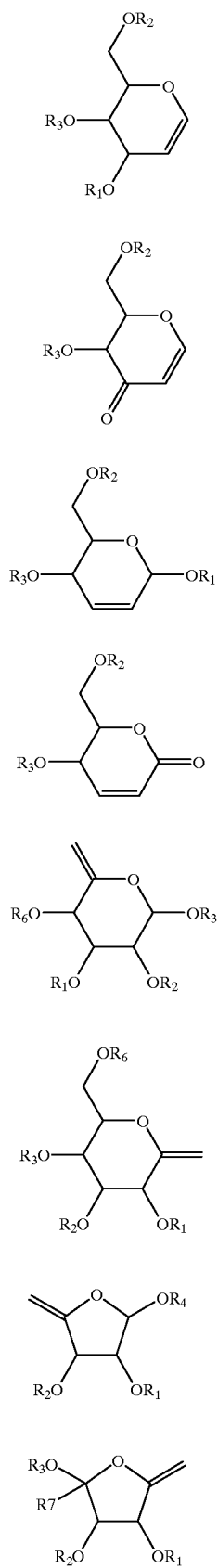
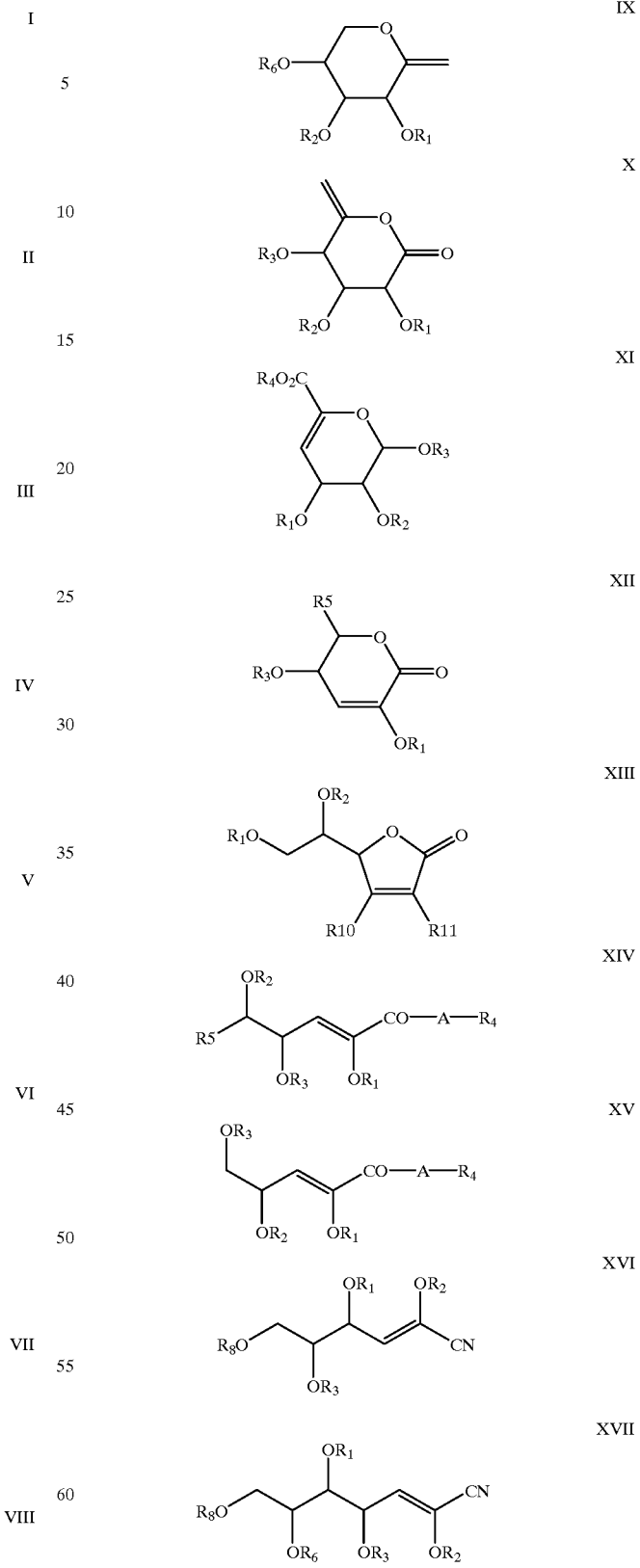
wherein $R_1$, $R_2$, $R_6$ and $R_8$, independently of each other, represent a hydrogen, alkyl, aralkyl, acyl or silyl group or each pair of the foregoing groups represent a common alkylidene group in a suitable spatial configuration; $R_3$ represents one of the foregoing groups or glycosyl; $R_4$ and $R_9$ represent hydrogen, alkyl or a counter ion; $R_5$ represents hydrogen, $CH_2OR_8$ or $COOR_9$; $R_7$ stands for hydrogen or O-glycosyl; $R_{10}$ and $R_{11}$ represents, independently of each other, a hydroxyl, acetamido, O-acyl or O-alkyl group and A stands for oxygen, an NH group or an N-alkyl group, and wherein said alkyl groups contain from 1 to 24 carbon atoms.

5. The hair treatment composition as defined in claim 1, containing said at least one copolymer and wherein said at least one copolymer is built up from said at least one monomer and at least one additional monomer, and wherein said at least one additional monomer is not derived from any saccharide and is radically polymerizable.

6. The hair treatment composition as defined in claim 5, wherein said at least one copolymer is made by a method comprising polymerizing 3,4,5-tri-O-benzoyl-1-deoxy-2,6-anhydro-D-fructose-hex-1-enitol and maleic acid anhydride and subsequently hydrolyzing benzoyl and anhydride groups present.

7. The hair treatment composition as defined in claim 5, wherein said at least one copolymer is made by a method comprising polymerizing 2,4,6-tri-O-acetyl-3-deoxy-D-erythro-hex-2-enono-1,5-lactone and vinyl acetate in a ratio of 21:79, or polymerizing 2,4,6-tri-O-acetyl-3-deoxy-D-erythro-hex-2-enono-1,5-lactone and vinyl pyrrolidone in a ratio of 45:55, or polymerizing 2,4,6-tri-O-acetyl-3-deoxy-D-erythro-hex-2-enono-1,5-lactone and butyl vinyl ether in a ratio of 50:50.

8. A hair treatment composition comprising a cosmetic carrier;

from 0.01 to 25% by weight of at least one polymer or copolymer made from at least one monomer, said at least one monomer being selected from the group consisting of ethylenic unsaturated saccharides, ethylenic unsaturated saccharic acids, derivatives of ethylenic unsaturated saccharides and derivatives of ethylenic unsaturated saccharic acids; and at least one film-forming polymer;

wherein said unsaturated sachharides and saccharic acids are present in cyclic or open chain form.

9. The hair treatment composition as defined in claim 8, containing from 0.01 to 25 percent by weight of said at least one film-forming polymer.

10. A method of treating hair comprising the steps of:

a) providing a hair treatment composition comprising a cosmetic carrier; and from 0.01 to 25% by weight of at least one polymer or copolymer made from at least one monomer, said at least one monomer being selected from the group consisting of ethylenic unsaturated saccharides, ethylenic unsaturated saccharic acids, derivatives of ethylenic unsaturated saccharides and derivatives of ethylenic unsaturated saccharic acids, wherein said unsaturated sachharides and saccharic acids are present in cyclic or open chain form; and b) applying said hair treatment composition to the hair in an amount sufficient for treating the hair.

11. The hair treatment composition as defined in claim 1, 8 or 10, wherein said cosmetic carrier includes water or ethanol and at least one additive ingredient selected from the group consisting of combability-improving agents, silicone oils, thickeners, perfume oils, turbidity-inducing agents, anionic surfactants, cationic surfactants, nonionic surfactants, amphoteric surfactants, moisturizing agents, dye stuffs, light-protective agents, antioxidants, luster-imparting agents and preservatives.

* * * * *